(12) United States Patent
Murphy

(10) Patent No.: US 8,888,784 B1
(45) Date of Patent: Nov. 18, 2014

(54) DUAL BLADED SURGICAL SAW AND METHOD OF USE

(76) Inventor: Christopher B. Murphy, Edgewater, FL (US)

( * ) Notice: Subject to any disclaimer, the term of this patent is extended or adjusted under 35 U.S.C. 154(b) by 146 days.

(21) Appl. No.: 13/597,851

(22) Filed: Aug. 29, 2012

(51) Int. Cl.
*A61B 17/00* (2006.01)

(52) U.S. Cl.
USPC .............................................. 606/82; 606/171

(58) Field of Classification Search
CPC ................................. A61B 17/148; B26B 3/04
USPC ................ 606/79, 82, 171; 30/369, 208, 266, 30/279.2, 299, 303, 302, 304; 173/214
See application file for complete search history.

(56) References Cited

U.S. PATENT DOCUMENTS

| | | | |
|---|---|---|---|
| H571 H | 2/1989 | Hollinger et al. | |
| 5,470,335 A | 11/1995 | Du Toit | |
| 6,007,541 A | 12/1999 | Scott | |
| 6,860,886 B1 | 3/2005 | Lee | |
| 7,744,616 B2 | 6/2010 | O'Donoghue | |
| 2004/0243136 A1 | 12/2004 | Gupta et al. | |
| 2011/0230887 A1 | 9/2011 | Bickenbach | |

OTHER PUBLICATIONS

MicroAire Series 7000 Oscillating Saw, Battery Electric (2 pages).
MicroAire Oscillating Saw, Pneumatic, Hall Connector (2 pages).
MicroAire Large Power Oscillating Saw Blades (1 page).

*Primary Examiner* — Andrew Yang
(74) *Attorney, Agent, or Firm* — Allen, Dyer, Doppelt, Milbrath & Gilchrist

(57) ABSTRACT

A dual bladed surgical saw and method of use. Two blade assemblies are attached to a saw body. Each blade assembly includes an oscillator driving a blade, and teeth on each blade. The blades are disposed at a pre-determined blade angle relative to each other, thus allowing two cuts to be made simultaneously and independently at the blade angle relative to each other. The blade assemblies may be rotatable relative to each other, which allows the pre-set blade angle to be varied appropriate to the procedure contemplated. One embodiment uses a slotted protractor bearing protractor indicia, and a threaded fastener to set the blade angle. Another embodiment uses shims between blade assembly arms to quickly and accurately set the blade angle. Method steps include pre-setting the blade angle, and making two cuts simultaneously at an angle relative to each other equal to the blade angle.

16 Claims, 6 Drawing Sheets

Sect. IV - IV

DUAL BLADED SURGICAL SAW AND METHOD OF USE

BACKGROUND OF THE INVENTION

1. Field of the Invention

This invention relates to surgical saws, and in particular to a dual bladed surgical saw and method of use.

2. Background of the Invention

Certain surgical procedures require bone cuts at precise angles. For example, the most common bunion surgical procedure is the Austin bunionectomy, also known as the Chevron bunionectomy.

The Austin bunionectomy procedure requires cutting a sixty degree angled cut into the first metatarsal head. The two resultant sections of the first metatarsal head are translated sideways, and then fixated. Fixation may be accomplished with a K-wire, pin, or other appropriate fixation device. Protruding sections of bone are cut off as appropriate, and a wedge may be removed from the first phalange as necessary. After the bones involved are aligned properly, they may be fixated with pins, screws, staples, etc., as appropriate.

The optimal angle at which to make the Austin bunionectomy angle cut is sixty degrees, that is to say, two cuts disposed at sixty degrees to each other. More than sixty degrees results in a loss of stability, while with less than sixty degrees one gets into the spike area, and healing surface area is sacrificed. Therefore it is important to achieve a sixty degree bone cut for best results from the procedure.

Existing Designs.

Currently, a first cut is made, and then a guide, which could be a guide wire, is used to make the second cut. This procedure is less than ideal, because it is time-consuming and not extremely accurate. Thus, it would be desirable to provide a dual bladed surgical saw whose two blades simultaneously make a pair of cuts at sixty degrees relative to each other. This ability would improve efficientcy as well as accuracy.

Further, it would be desirable to be able to vary the angle between the two blades, in order to make other bone cuts necessary during surgery. For instance, it would be helpful to be able to make two bone cuts simultaneously to isolate a bone wedge for removal. Such cuts typically require a pair of bone cuts at an angle of ten to thirty degrees relative to each other.

Other angled bone cuts which would benefit from a dual bladed surgical saw include hand procedures. It would be beneficial to provide a dual bladed surgical saw whose blades could be pre-set to the correct angle for the procedure, and then both cuts made simultaneously and independently by the two blades at precisely the correct angle.

It would also be desirable to be able to remove one blade from the dual bladed surgical saw to leave only one blade. This blade could be used conventionally for cuts where only one blade is required.

A number of dual bladed surgical saws have been proposed. U.S. Pat. Nos. 7,744,616 and 6,007,541, Publication No. 2011/0230887, and Statutory Invention Registration H571 by O'Donoghue, Scott, Bickenbach, and Hollinger et al. respectively, all described saws having two blades. These designs all taught two parallel blades, with no provision for changing the angle between them. Thus, these would not be able to make the sixty degree cuts required during Austin bunionectomies, nor the ten to thirty degree angled cuts required for bone wedge removal, nor the other angled cuts required by other procedures.

U.S. Pat. No. 6,860,886 was granted Lee for a reciprocating surgical saw having a single blade whose angle relative to the handle was adjustable. While this design disclosed angular adjustability of the single blade, it did not disclose a single saw having two blades, nor adjustability of the angle between the two blades. Thus, the Lee device would not serve to make the sixty degree cuts required during Austin bunionectomies, nor the ten to thirty degree angled cuts required for bone wedge removal, nor the other angled cuts required by other procedures.

SUMMARY OF THE INVENTION

Accordingly, it is an object of the present invention to provide a dual bladed surgical saw and method of use which is capable of simultaneously making two cuts at a pre-determined angle. Design features allowing this object to be accomplished include a saw body having a switch which actuates a first oscillator and a second oscillator, a saw blade attached to each oscillator, and a blade angle between the saw blades. Advantages associated with the accomplishment of this object include increased accuracy and efficiency in the surgical procedure.

It is another object of the present invention to provide a dual bladed surgical saw and method of use which is capable of simultaneously making two cuts at a pre-determined angle, which angle may be varied prior to making the cuts. Design features allowing this object to be accomplished include a saw body having a switch which actuates a first oscillator and a second oscillator which are part of a first blade assembly and a second blade assembly, a rotatable attachment between the two blade assemblies, a saw blade attached to each oscillator, an arm attached to each blade assembly, and a protractor or shims between the arms. Benefits associated with the accomplishment of this object include the ability to pre-set an angle between the cuts made by the blades to suit the specific surgical procedure being performed, increased accuracy and improved efficiency.

It is still another object of this invention to provide a dual bladed surgical saw and method of use which permits the removal of one blade assembly. Design features enabling the accomplishment of this object include a first blade assembly rotatably attached to a second blade assembly. An advantage associated with the realization of this object is the ability to remove the first blade assembly and use the surgical saw with only one blade, thus increasing the versatility and ease of use of the dual bladed surgical saw.

It is yet another object of this invention to provide a dual bladed surgical saw and method of use which is inexpensive to produce. Design features allowing this object to be achieved include the use of commercially available components. Benefits associated with reaching this objective include reduced cost, and hence increased availability.

BRIEF DESCRIPTION OF THE DRAWINGS

The invention, together with the other objects, features, aspects and advantages thereof will be more clearly understood from the following in conjunction with the accompanying drawings.

Six sheets of drawings are provided. Sheet one contains FIG. 1. Sheet two contains FIG. 2. Sheet three contains FIGS. 3 and 4. Sheet four contains FIG. 5. Sheet five contains FIG. 6. Sheet six contains FIGS. 7-9.

DETAILED DESCRIPTION OF THE PREFERRED EMBODIMENT

Figure 1:
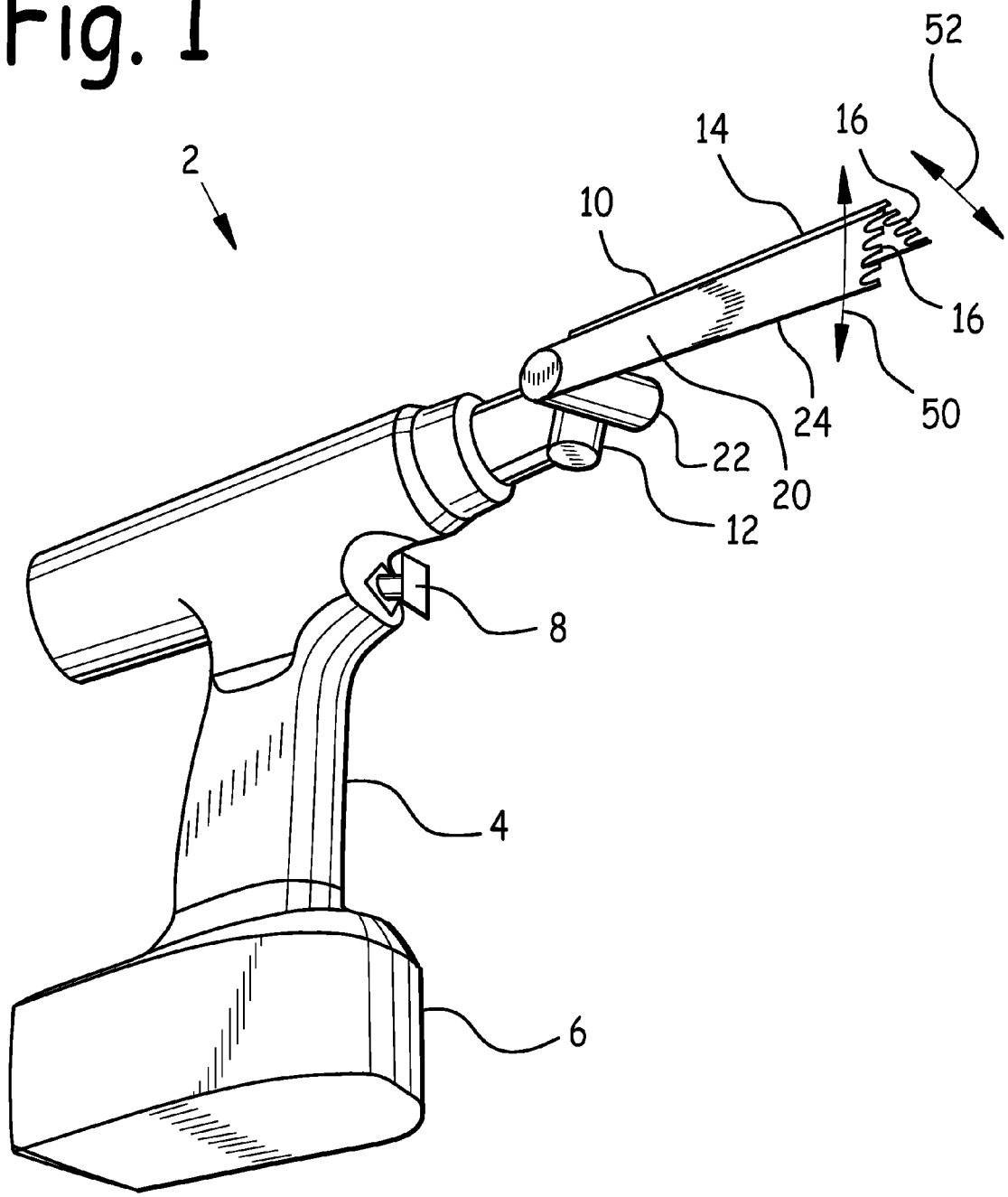
FIG. 1 is a right side isometric view of a dual bladed surgical saw.

Referring now to FIG. 1, we observe a right side isometric view of dual bladed surgical saw 2. Dual bladed surgical saw 2 incorporates first blade assembly 10 and second blade assembly 20 attached to saw body 4. First blade assembly 10 includes first blade 14 attached to first oscillator 12 at one end, and has saw teeth 16 at the other. Second blade assembly 20 includes second blade 24 attached to second oscillator 22 at one end, and has saw teeth 16 at the other.

In the example illustrated in FIG. 1, saw body 4 is an electric saw body with battery 6 connected to first blade assembly 10 and second blade assembly 20 through switch 8. When switch 8 is closed, first oscillator 12 and second oscillator 22 oscillate, which in turn cause first blade 14 and second blade 24 to reciprocate as indicated by arrows 50 and 52. While some of the figures herein depict electric saw bodies 4, it is intended to fall within the scope of this disclosure that any appropriate saw body and oscillators be used, including electric, pneumatic, etc.

First blade 14 and second blade 24 are disposed at blade angle 30 relative to each other. In the embodiment dual bladed surgical saw 2 depicted in FIG. 1, blade angle 30 is fixed at a pre-determined value. This may be desirable where dual bladed surgical saw 2 is used for a single procedure, or group of procedures, which require the same cut angle. For example, if dual bladed surgical saw 2 is to be used solely for Austin bunionectomies, blade angle 30 would be fixed at sixty degrees during the manufacturing of dual bladed surgical saw 2. If it is desired to be able to vary blade angle 30, alternate embodiments of dual bladed surgical saw 2 with that capability are disclosed herein, and are described below in connection with FIGS. 3-5.

Figure 2:
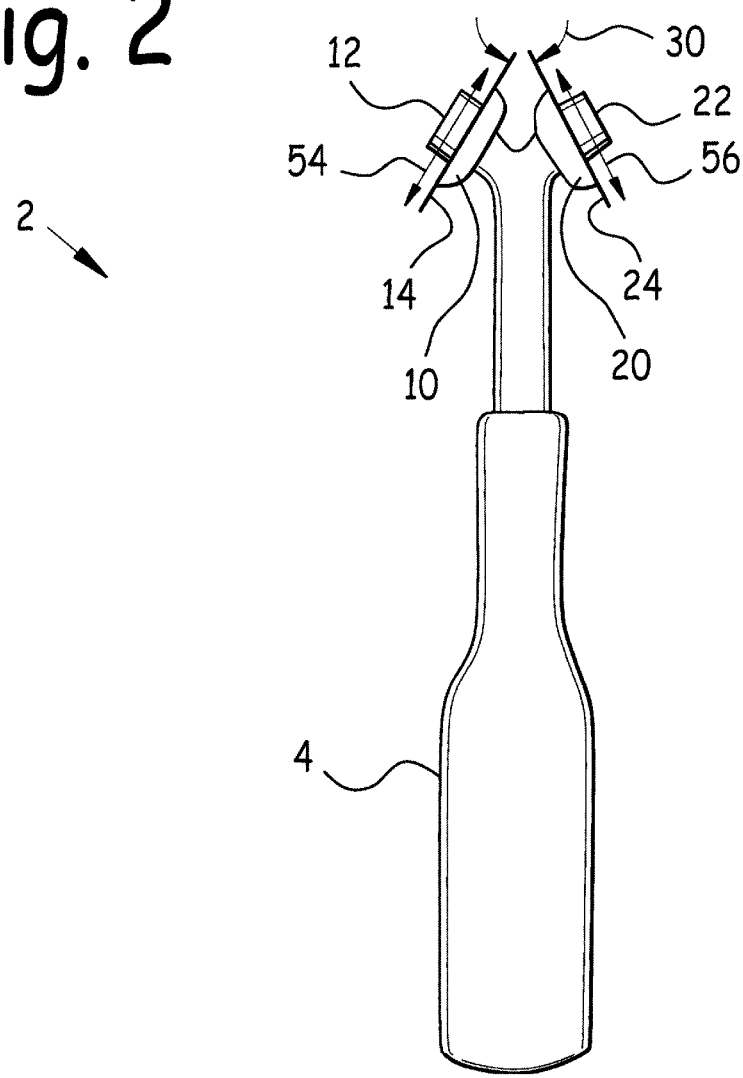
FIG. 2 is a rear isometric view of a dual bladed surgical saw.

FIG. 2 is a rear isometric view of an alternate embodiment dual bladed surgical saw 2. The dual bladed surgical saw 2 depicted in FIG. 2 includes a blade angle 30 between first blade 14 and second blade 24 which is fixed. First oscillator 12 drives first blade 14, and second oscillator 22 drives second blade 24 as indicated by arrows 54 and 56.

Figure 3:
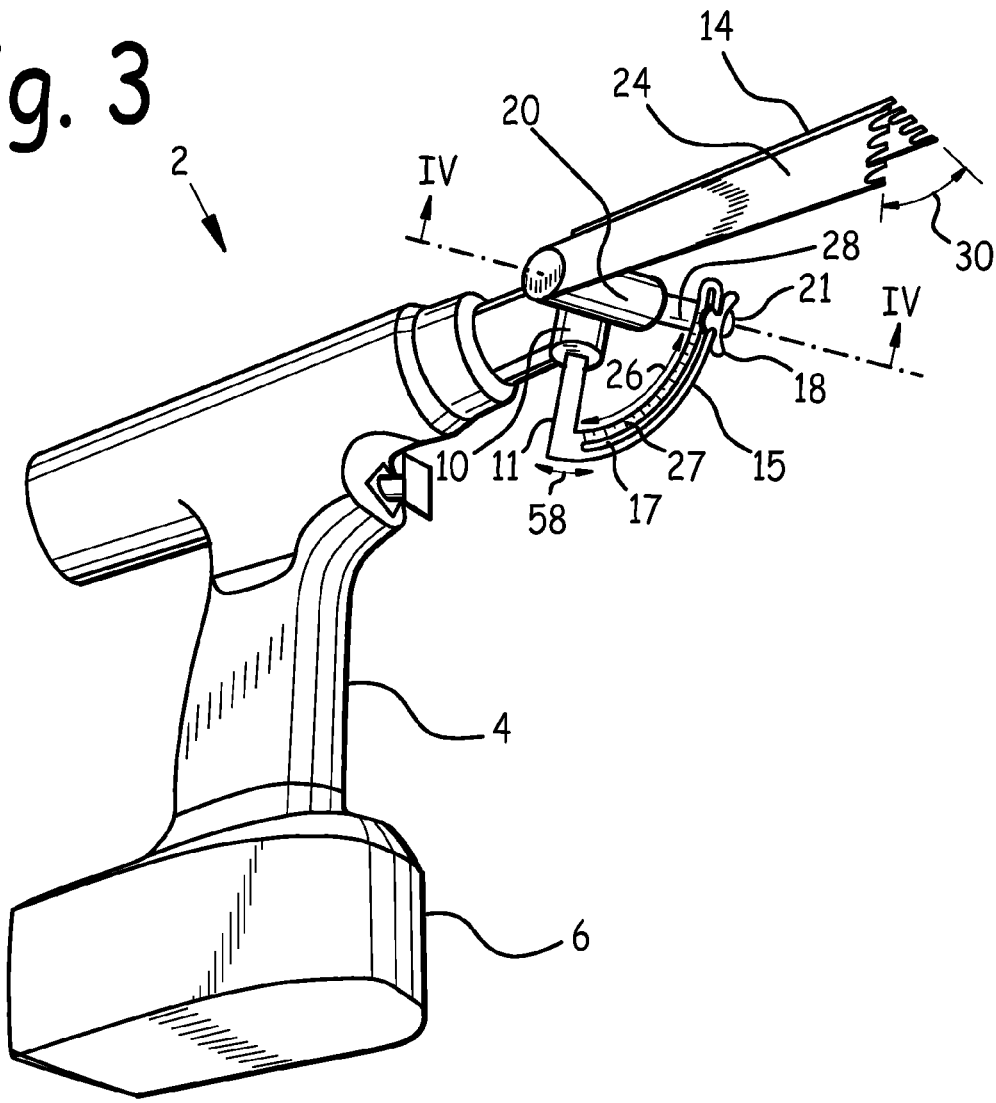
FIG. 3 is a right side isometric view of a dual bladed surgical saw with a protractor being used to set the angle between the blades.

FIG. 3 is a right side isometric view of a variable blade angle 30 dual bladed surgical saw 2 with protractor 15 being used to set the blade angle 30 between first blade 14 and second blade 24. First blade assembly arm 11 is attached to, and extends from, first blade assembly 10. Second blade assembly arm 21 is attached to, and extends from, second blade assembly 20. Protractor 15 is shaped substantially as an arc of a circle, and as attached at one end to first blade assembly arm 11. Protractor 15 includes protractor slot 17 disposed along the length of protractor 15. Protractor slot 17 is also shaped substantially as an arc of a circle.

Figure 4:
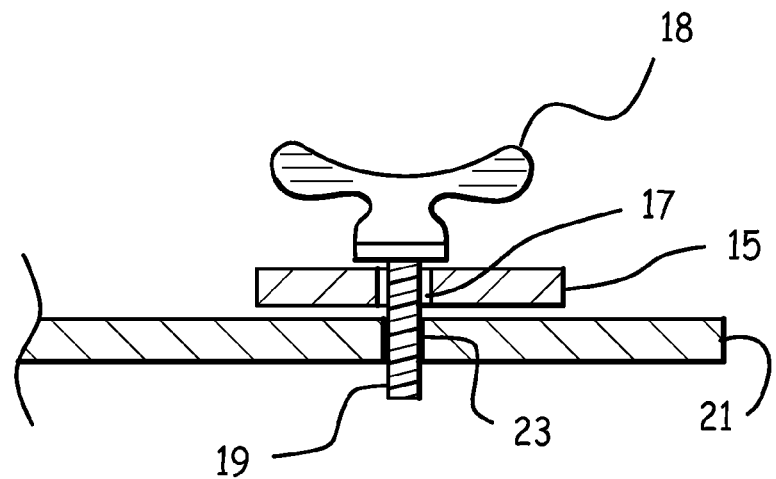
FIG. 4 is a side cross-sectional view of a fastener, protractor, and second blade assembly arm taken at section IV-IV of FIG. 3.

FIG. 4 is a side cross-sectional view of fastener 18, protractor 15, and second blade assembly arm 21 taken at section IV-IV of FIG. 3. Fastener 18 has fastener threaded stud 19, and serves to releasably fix the position of protractor 15 relative to second blade assembly arm 21. Second blade assembly arm 21 incorporates second blade assembly arm threaded bore 23, sized to mate with fastener threaded stud 19. Fastener threaded stud 19 is sized to slidably fit through protractor slot 17.

Protractor indicia 27 is inscribed along the length of protractor 15 to aid in setting blade angle 30. Protractor 15 is attached to first blade assembly arm 11 in a position such that protractor angle 26 read from protractor indicia 27 equals blade angle 30. Protractor angle 26, as read on protractor indicia 27, may be defined by the location of fastener 18 along the length of protractor 15, by reference to index line 28 on second blade assembly arm 21, or any other appropriate reference.

In use, fastener threaded stud 19 is inserted through protractor slot 17 and threaded loosely into second blade assembly arm threaded bore 23. Blade angle 30 is set as desired by rotating first blade assembly arm 11 relative to second blade assembly arm 21 as indicated by arrow 58 in FIG. 3. When the desired blade angle 30 is achieved, fastener 18 is tightened into second blade assembly arm threaded bore 23, thus entrapping protractor 15 between fastener 18 and second blade assembly arm 21, thus immobilizing protractor 15 relative to second blade assembly arm 21 and fixing blade angle 30. Protractor indicia 27 corresponds to blade angle 30, and may be used as explained above to aid in the determination of blade angle 30.

While FIGS. 3 and 4 depict protractor 15 attached to first blade assembly arm 11 and a threaded bore in second blade assembly arm 21, it is intended to fall within the scope of this disclosure that protractor 15 could as easily be attached to second blade assembly arm 21 and that the threaded bore be disposed in first blade assembly arm 11.

Figure 5:
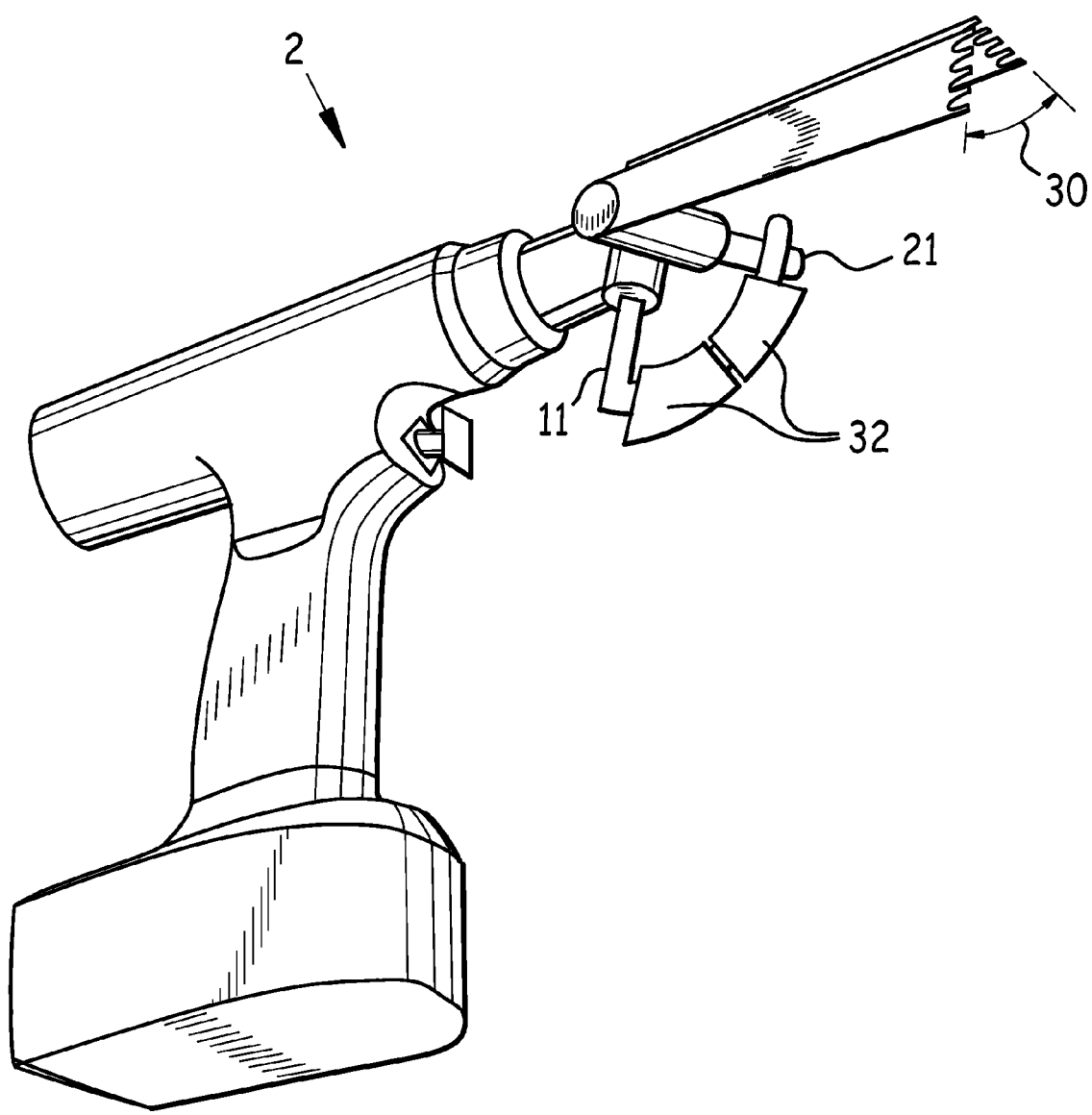
FIG. 5 is a right side isometric view of a dual bladed surgical saw with shims being used to set the angle between the blades.

FIG. 5 is a right side isometric view of an alternate embodiment dual bladed surgical saw 2 with shims 32 being used to set blade angle 30. In this embodiment, shims 32 are inserted between first blade assembly arm 11 and second blade assembly arm 21 as appropriate to achieve the blade angle 30 desired. The use of shims 32 is especially useful where a pre-determined blade angle 30, such as sixty degrees, is desired, and can be achieved quickly and easily by insertion of the appropriately sized shim(s) 32.

Figure 6:
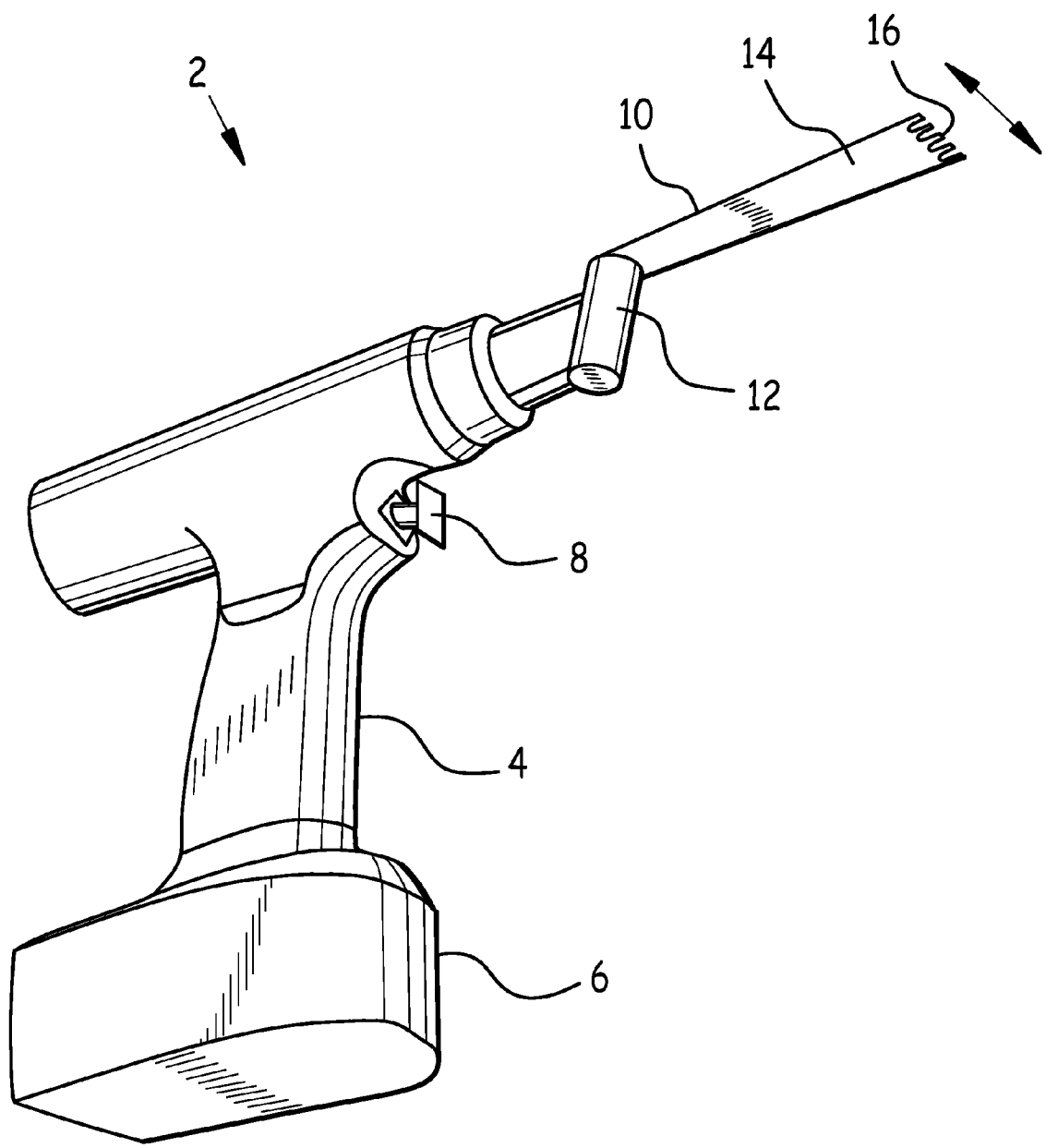
FIG. 6 is a right quarter side isometric view of a dual bladed surgical saw with one blade assembly removed.

FIG. 6 is a right quarter side isometric view of an alternate embodiment dual bladed surgical saw 2 with one blade assembly removed, in this case second blade assembly 20. A single blade assembly remains (in this case first blade assembly 10 having first blade 14) for use in conventional, single bladed surgical saw fashion.

Figure 7:
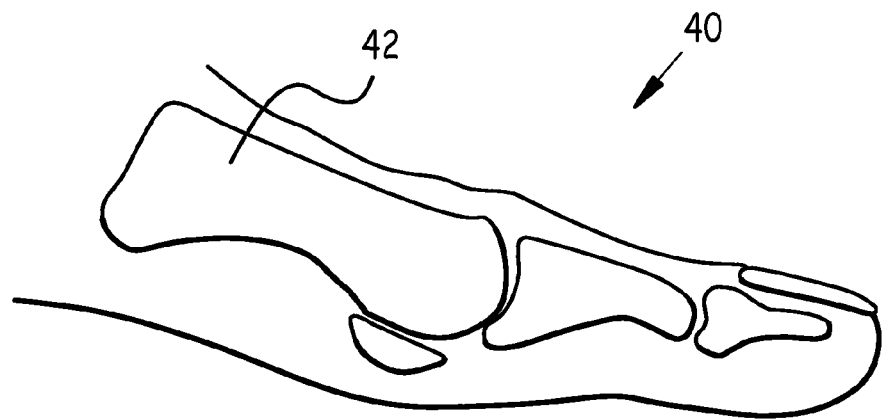
FIGS. 7-9 depict the method of use for a dual bladed surgical saw.
Figure 8:
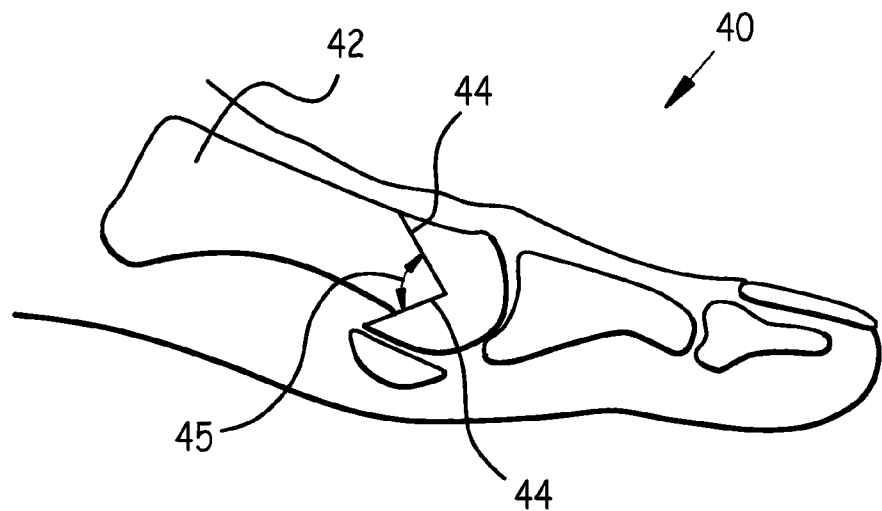
Figure 9:
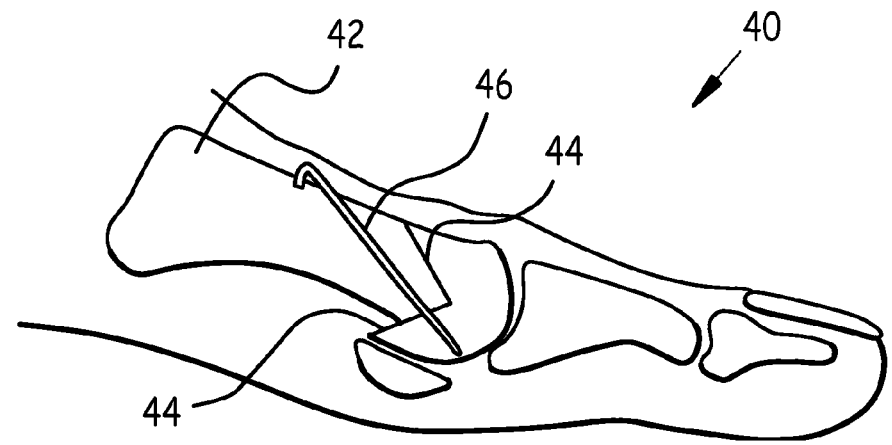

FIGS. 7-9 depict the method of use for a dual bladed surgical saw 2 during an Austin bunionectomy on foot 40. Blade angle 30 is set appropriate to the procedure, dual bladed surgical saw 2 is started, then the cuts are made by first blade 14 and second blade 24 at cut angle 45, which is equal to blade angle 30. In the example illustrated in FIGS. 7-9, cuts 44 are made in the head of metatarsal 42. The bone is then fixed in place using appropriate fixation devices (K-wire 46 in FIG. 9), and the procedure concluded in conventional manner.

Thus, the instant method of use for a dual bladed surgical saw includes the steps of:

A. Providing a dual bladed surgical saw comprising a saw body; a first blade assembly attached to the saw body; and a second blade assembly attached to the saw body; the first blade assembly comprising a first oscillator driving a first blade, and saw teeth at and end of the first blade opposite the first oscillator; the second blade assembly comprising a second oscillator driving a second blade, and saw teeth at and end of the second blade opposite the second oscillator; the first blade being disposed at a pre-determined blade angle relative to the second blade;

B. Starting the saw whereby the first oscillator causes the first blade to reciprocate, and the second oscillator causes the second blade to reciprocate; and C. Using the first blade and the second blade to simultaneously make two cuts at the blade angle relative to each other.

The instant method of use for a dual bladed surgical saw may include the further steps of pre-setting the blade angle at substantially sixty degrees; and using the dual bladed surgical saw to make two cuts in a first metatarsal bone at substantially sixty degrees relative to each other.

The instant method of use for a dual bladed surgical saw may include the further steps of providing means of rotating the first blade assembly relative to the second blade assembly; setting a blade angle between the first blade and the second blade; and making cuts at a cut angle relative to each other which equals the pre-set blade angle.

The instant method of use for a dual bladed surgical saw may include the further steps of providing a blade assembly arm attached to each of the blade assemblies, providing a protractor attached to one of the blade assembly arms and a threaded bore in the other blade assembly arm; providing a protractor slot in the protractor; providing a fastener having a threaded stud sized to slidably fit through the protractor slot and mate with the threaded bore; sliding the threaded stud through the protractor slot and threading the threaded stud loosely into the threaded bore, rotating one blade assembly relative to the other blade assembly until a desired blade angle is achieved; and tightening the threaded stud into the threaded bore, thereby releasably fixing the blade angle.

The instant method of use for a dual bladed surgical saw may include the further steps of providing protractor indicia on the protractor; and using the protractor indicia to aid in setting the desired blade angle.

The instant method of use for a dual bladed surgical saw may include the further steps of providing a blade assembly arm attached to each of the blade assemblies; providing at least one shim; rotating one blade assembly relative to the other blade assembly until a desired blade angle is achieved; and emplacing the at least one shim between the blade assembly arms, thereby releasably fixing the blade angle.

The instant method of use for a dual bladed surgical saw may include the further steps of providing a blade assembly which is removable from the dual bladed surgical saw; removing the removable blade assembly from the dual bladed surgical saw; and operating the dual bladed surgical saw in conventional fashion as a single bladed surgical saw.

In the preferred embodiment, saw body 4, first oscillator 12, first blade 14, second oscillator 22, and second blade 24 were commercially available items. Protractor 15, first blade assembly arm 11 and second blade assembly arm 21 were made of metal, stainless steel, synthetic, plastic, or other appropriate material. Fastener 18 was a commercially available fastener.

While a preferred embodiment of the invention has been illustrated herein, it is to be understood that changes and variations may be made by those skilled in the art without departing from the spirit of the appending claims.

DRAWING ITEM INDEX

2 dual bladed surgical saw
4 saw body
6 battery
8 switch
10 first blade assembly
11 first blade assembly arm
12 first oscillator
14 first blade
15 protractor
16 teeth
17 protractor slot
18 fastener
19 fastener threaded stud
20 second blade assembly
21 second blade assembly arm
22 second oscillator
23 second arm assembly threaded bore
24 second blade
26 protractor angle
27 protractor indicia
28 index line
30 blade angle
32 shim
40 foot
42 first metatarsal
44 cut
45 cut angle
46 K-wire
50 arrow
52 arrow
54 arrow
56 arrow
58 arrow

I claim:

1. A dual bladed surgical saw comprising:
    a saw body;
    a first blade assembly having a first blade attached to said saw body;
    a second blade assembly having a second blade attached to said saw body;
    said first blade assembly comprising a first oscillator driving said first blade, and saw teeth at an end of said first blade opposite said first oscillator;
    said second blade assembly comprising a second oscillator driving said second blade, and saw teeth at an end of said second blade opposite said second oscillator;
    said first blade being disposed at a pre-determined blade angle relative to said second blade;
    means of rotating said first blade assembly relative to said second blade assembly; and means of fixing said blade angle.

2. The dual bladed surgical saw of claim 1 wherein said means of fixing said blade angle comprises a blade assembly arm attached to each said blade assembly, a protractor attached to one said blade assembly arm and a threaded bore in another said blade assembly arm, a protractor slot in said protractor, and a fastener having a threaded stud sized to fit slidably through said protractor slot and mate with said threaded bore, said threaded stud being slidably disposed through said protractor slot and threaded into said threaded bore.

3. The dual bladed surgical saw of claim 2 further comprising protractor indicia on said protractor, whereby said protractor indicia may be used to aid in setting said blade angle.

4. The dual bladed surgical saw of claim 3 further comprising an index line on the said blade assembly arm in which said threaded bore is disposed, whereby said blade angle may be more accurately set.

5. The dual bladed surgical saw of claim 1 wherein said means of fixing said blade angle comprises a blade assembly arm attached to each said blade assembly, and at least one shim disposed between said blade assembly arms, whereby said blade angle may be quickly and easily set.

6. The dual bladed surgical saw of claim 1 wherein one said blade assembly is removable from said dual bladed surgical saw.

7. The dual bladed surgical saw of claim 1 wherein said dual bladed surgical saw is electrically actuated.

8. The dual bladed surgical saw of claim 1 wherein said dual bladed surgical saw is pneumatically actuated.

9. A method of use for a dual bladed surgical saw comprising the steps of:

A. Providing a dual bladed surgical saw comprising a saw body;

a first blade assembly attached to said saw body;

and a second blade assembly attached to said saw body;

said first blade assembly comprising a first oscillator driving a first blade, and saw teeth at an end of said first blade opposite said first oscillator;

said second blade assembly comprising a second oscillator driving a second blade, and saw teeth at an end of said second blade opposite said second oscillator;

said first blade being disposed at a pre-determined blade angle relative to said second blade;

B. Starting said saw whereby said first oscillator causes said first blade to reciprocate, and said second oscillator causes said second blade to reciprocate; and C. Using said first blade and said second blade to simultaneously make two cuts at a cut angle relative to each other equal to said blade angle.

10. The method of use for a dual bladed surgical saw of claim 9 comprising the further steps of providing a patient having a patient bone, and making said cuts in said patient bone.

11. The method of use for a dual bladed surgical saw of claim 10 comprising the further steps of providing a patient bone with is a first metatarsal bone; pre-setting said blade angle at substantially sixty degrees; and using said dual bladed surgical saw to make two cuts in said first metatarsal bone at a cut angle of substantially sixty degrees relative to each other.

12. The method of use for a dual bladed surgical saw of claim 9 comprising the further steps of providing means of rotating said first blade assembly relative to said second blade assembly; rotating said first blade assembly relative to said second blade assembly until achieving a desired blade angle between said first blade assembly and said second blade assembly; and making cuts which are at said pre-set blade angle relative to each other.

13. The method of use for a dual bladed surgical saw of claim 12 comprising the further steps of providing a blade assembly arm attached to each said blade assembly, providing a protractor attached to one said blade assembly arm and a threaded bore in another said blade assembly arm; providing a protractor slot in said protractor; providing a fastener having a threaded stud sized to fit slidably through said protractor slot and mate with said threaded bore; sliding said threaded stud through said protractor slot and threading said threaded stud loosely into said threaded bore; rotating one blade assembly relative to another said blade assembly until a desired blade angle is achieved; and tightening said threaded stud into said threaded bore, thereby releasably fixing said blade angle.

14. The method of use for a dual bladed surgical saw of claim 13 comprising the further steps of providing protractor indicia on said protractor; and using said protractor indicia to aid in setting said desired blade angle.

15. The method of use for a dual bladed surgical saw of claim 12 comprising the further steps of providing a blade assembly arm attached to each said blade assembly; providing at least one shim; rotating one blade assembly relative to another said blade assembly until a desired blade angle is achieved; and emplacing said at least one shim between said blade assembly arms, thereby releasably fixing said blade angle.

16. The method of use for a dual bladed surgical saw of claim 9 comprising the further steps of providing one said blade assembly which is removable from said dual bladed surgical saw; removing said removable blade assembly from said dual bladed surgical saw; and operating said dual bladed surgical saw in conventional fashion as a single bladed surgical saw.

\* \* \* \* \*